United States Patent [19]

Nguyen

[11] Patent Number: 5,073,367

[45] Date of Patent: Dec. 17, 1991

[54] METHOD FOR INCREASING THE PRODUCTIVITY OF SOWS

[75] Inventor: Tan H. Nguyen, Le Porlair, France

[73] Assignee: Guyomarc'h Nutrition Animale, Elven, France

[21] Appl. No.: 347,409

[22] Filed: May 4, 1989

[30] Foreign Application Priority Data

May 9, 1988 [FR] France .................................. 88 06215

[51] Int. Cl.⁵ .............................................. A61K 39/07
[52] U.S. Cl. ..................................... 424/93; 435/252.5
[58] Field of Search ......................... 435/252.5; 424/93

[56] References Cited

PUBLICATIONS

Graebner Med. Klin., 64 (1989) No. 23, pp. 1080–1084.
Pillen, Med. Klin. 22(7) 1971, pp. 266–268.

Primary Examiner—Howard E. Schain
Assistant Examiner—Choon Koh
Attorney, Agent, or Firm—Dressler, Goldsmith, Shore, Sutker & Milnamow, Ltd.

[57] ABSTRACT

The present invention relates to a new method for increasing the productivity of sows.

In the method according to the invention, Bacillus IP 5832 and/or its spores is/are administered orally to breeding sows.

3 Claims, No Drawings

METHOD FOR INCREASING THE PRODUCTIVITY OF SOWS

The present invention relates to a method for increasing the productivity of sows.

In every country in the world, infantile mortality of piglets is one of the main factors holding back the productivity of pig farms.

The causes of this mortality of piglets are manifold, and do not always fall within the category of infectious diseases, as shown by the results of this survey, quoted by the journal "L'Eleveur de Porcs" (Pig Breeder) (October 1982, No. 139, page 23):

| CAUSES OF MORTALITY BEFORE WEANING (expressed in % of piglets) | |
| --- | --- |
| Stillborn | 1.6 |
| During farrowing | 4.5 |
| Insufficient development | 3.5 |
| Injury/crushing | 4.0 |
| Digestive diseases | 2.0 |
| Pneumonia | 0.6 |
| Septicemia | 0.9 |
| Malformations | 1.1 |
| Polyarthritis | 1.1 |
| Various diseases | 2.4 |
| Causes not determined | 0.5 |
| | 22.3 |

The vegetative spores of Bacillus IP 5832 are commercially available and have been used for a long time as an antidiarrhea drug in human medicine under the brand name BACTISUBTIL® (Dictionnaire VIDAL).

The present invention relates to the use of Bacillus IP 5832 and/or its spores in breeding sows, as a means for reducing the losses of their piglets and thus increasing the productivity of the sows.

Bacillus IP 5832 and/or its spores may be administered orally to the sows according to all techniques commonly used in pig breeding: mixed in the feed, dispersed in water, packaged in tables, in hard gelatin capsules, and the like.

Bacillus IP 5832 and/or its spores is/are administered to the sows before farrowing and then during suckling of the piglets.

The daily provision of Bacillus IP 5832 and/or its spores should be calculated according to the means of administration. They correspond, on average, to the normal intake by the sows of a complete feed for sows containing from 500,000 to 2,000,000 microorganisms per gram of feed.

The non-limiting examples which follow illustrate the invention.

EXAMPLE No. 1

28 perfectly healthy pregnant sows are distributed into two homogeneous batches 10 days before their presumed date of farrowing.

One batch (control) receives, from this date and, after farrowing, up to weaning of the piglets at 26 days, an experimental complete feed containing 87.2% of dry matter, 17.5% of protein, 4.7% of fat, 6.2% of cellulose and 6.9% of inorganic matter.

The second batch receives, during the same period, a feed of the same basic composition but containing Bacillus IP 5832 in the proportion of 797,000 revitalizable microorganisms per gram of feed.

The piglets do not have access to the sows' feeds.

The mean results obtained were as follows:

| | CONTROL (1) | IP 5832 (2) | DIFFERENCE$_{(2)}$ (%) $\overline{(1)}$ |
| --- | --- | --- | --- |
| NUMBER OF SOWS | 12* | 14 | — |
| TOTAL PIGLETS BORN/SOW | 10.25 | 10.93 | — |
| PIGLETS STILLBORN/SOW | 0.83 | 0.64 | −22.89 |
| PIGLETS LIVE-BORN/SOW | 9.42 | 10.29 | +9.24 |
| PIGLETS WEANED/SOW | 8.33 | 9.43 | +13.21 |
| MORTALITY AT BIRTH (%) | 8.10 | 5.86 | −27.65 |
| MORTALITY OF THE LIVE-BORN PIGLETS, FROM BIRTH TO WEANING (%) | 11.57 | 8.36 | −27.74 |
| TOTAL LOSSES/TOTAL PIGLETS BORN (%) | 18.73 | 13.72 | −26.75 |
| CONSUMPTION OF FEED PER SOW (kg) | 147.0 | 142.6 | — |

*2 sows eliminated from the trial. 1 due to agalactia and 1 due to sudden death.

EXAMPLE No. 2

32 clinically healthy sows are divided into two homogeneous batches one week before their presumed date of farrowing.

A first batch receives, from the distribution and throughout the period of suckling the piglets (26 days), a commercial complete feed containing 86.5% of dry matter, 17.6% of protein, 3.7% of fat, 5.9% of cellulose and 6.1% of inorganic matter. This first batch serves as a control.

The second batch receives, during the same period, the same basic feed supplemented with Bacillus IP 5832 in the proportion of 1,200,000 revitalizable microorganisms per gram of feed.

The piglets do not have access to the sows' feeds.

The mean results obtained were as follows:

| | CONTROL (A) | IP 5832 (B) | DIFFERENCE $\frac{(B)}{(A)}$ (%) |
|---|---|---|---|
| NUMBER OF SOWS | 16 | 16 | — |
| TOTAL PIGLETS BORN/SOW | 11.81 | 11.13 | — |
| PIGLETS STILLBORN/SOW | 1.25 | 0.38 | −69.60 |
| PIGLETS LIVE-BORN/SOW | 10.56 | 10.75 | +1.80 |
| PIGLETS WEANED/SOW | 8.13 | 9.13 | +12.30 |
| MORTALITY AT BIRTH (%) | 10.58 | 3.41 | −67.77 |
| MORTALITY OF THE LIVE-BORN PIGLETS, FROM BIRTH TO WEANING (%) | 23.01 | 15.07 | −34.51 |
| TOTAL LOSSES/TOTAL PIGLETS BORN (%) | 31.16 | 17.97 | −42.33 |
| CONSUMPTION OF FEED PER SOW (kg) | 134.6 | 135.0 | — |

Although the absolute values of the improvements are different in the two examples, the trends obtained were identical.

The mechanisms of action of this new application of Bacillus IP 5832 and/or its spores remain unknown.

The invention is all the more novel for the fact that the sows in the two examples quoted were in perfect health, as specified above.

I claim:

1. A method for increasing the productivity of clinically healthy sows, wherein Bacillus IP 5832 and/or its spores is/are administered orally to breeding sows.

2. The method as claimed in claim 1, wherein Bacillus IP 5832 and/or its spores is/are administered to the sows before farrowing and during suckling of the piglets.

3. A method for increasing the productivity of clinically healthy sows wherein Bacillus IP 5832 and/or its spores is/are administered orally to breeding sows in a daily amount corresponding to the normal intake by the sows of a complete feed for sows containing 500,000 to 2,000,000 revitalizable microorganisms per gram of feed.

* * * * *